(12) United States Patent
Sultan

(10) Patent No.: US 10,568,727 B2
(45) Date of Patent: *Feb. 25, 2020

(54) SYSTEMS AND METHODS FOR ASSISTING PATIENTS IN EMPTYING THEIR BLADDER EFFICIENTLY

(71) Applicant: Sam Sultan, Pembroke Pines, FL (US)

(72) Inventor: Sam Sultan, Pembroke Pines, FL (US)

( * ) Notice: Subject to any disclaimer, the term of this patent is extended or adjusted under 35 U.S.C. 154(b) by 130 days.

This patent is subject to a terminal disclaimer.

(21) Appl. No.: 15/677,382

(22) Filed: Aug. 15, 2017

(65) Prior Publication Data

US 2018/0028301 A1 Feb. 1, 2018

Related U.S. Application Data

(63) Continuation of application No. 15/297,727, filed on Oct. 19, 2016, now Pat. No. 9,750,591.

(60) Provisional application No. 62/368,401, filed on Jul. 29, 2016.

(51) Int. Cl.
| | |
|---|---|
| *A61F 2/04* | (2013.01) |
| *A61B 5/20* | (2006.01) |
| *A61F 2/00* | (2006.01) |
| *A61B 5/03* | (2006.01) |

(52) U.S. Cl.
CPC .............. *A61F 2/0036* (2013.01); *A61B 5/03* (2013.01); *A61B 5/205* (2013.01); *A61F 2/042* (2013.01); *A61F 2250/0001* (2013.01); *A61F 2250/008* (2013.01)

(58) Field of Classification Search
CPC .............................. A61F 2/04; A61F 2002/044
USPC ............................................... 623/23.65–23.7
See application file for complete search history.

(56) References Cited

U.S. PATENT DOCUMENTS

| | | | |
|---|---|---|---|
| 3,810,259 | A | 5/1974 | Summers |
| 5,752,978 | A | 5/1998 | Chancellor |
| 5,833,595 | A | 11/1998 | Lin |
| 6,296,668 | B1 | 10/2001 | Desgrandchamps et al. |
| 6,393,323 | B1 | 5/2002 | Sawan et al. |
| 6,576,019 | B1 | 6/2003 | Atala |

(Continued)

FOREIGN PATENT DOCUMENTS

| | | |
|---|---|---|
| WO | WO 2015/125110 | 8/2015 |
| WO | WO 2015/159185 A1 | 10/2015 |
| WO | WO 2016/029159 | 2/2016 |

OTHER PUBLICATIONS

An Implant to Empty the Bladder or Close the Urethra [online]; [retrieved on Jul. 28, 2016]; Retrieved from http://www.ncbi.nlm.nih.gov/pmc/articles/PMC492703/pdf/jnnpsyc00154-0046.pdf.

(Continued)

*Primary Examiner* — Suzette J Gherbi

(74) *Attorney, Agent, or Firm* — Woodard, Emhardt, Henry, Reeves & Wagner, LLP; Charles Meyer

(57) ABSTRACT

The present disclosure relates generally to systems, components, devices and methods for assisting a patient to empty his or her weakened or paralyzed bladder or a neobladder efficiently. The system and method includes a pressure sensor for sensing the pressure in the urinary bladder of a patient and an alert mechanism which alerts the patient of the bladder fullness and the need to void. An actuating device is operably coupled to the system to selectively activate a compression assembly. When activated, the compression assembly compresses the bladder to permit emptying of the bladder.

14 Claims, 7 Drawing Sheets

(56) References Cited

U.S. PATENT DOCUMENTS

| | | | |
|---|---|---|---|
| 6,645,138 B2 | 11/2003 | Cook et al. | |
| 6,682,480 B1 | 1/2004 | Habib et al. | |
| 7,384,390 B2 | 6/2008 | Furness et al. | |
| 7,499,753 B2 | 3/2009 | Forsell | |
| 7,909,790 B2 | 3/2011 | Burnett | |
| 7,918,897 B2 | 4/2011 | Bertram et al. | |
| 8,160,710 B2 | 4/2012 | Buysman et al. | |
| 8,585,580 B2 | 11/2013 | Vaingast et al. | |
| 8,644,938 B2 | 2/2014 | Craggs | |
| 8,696,760 B2 | 4/2014 | Bertram et al. | |
| 8,725,249 B2 | 5/2014 | Bar-Yoseph et al. | |
| 9,101,314 B2 | 8/2015 | Shi | |
| 9,750,591 B1* | 9/2017 | Sultan | A61F 2/0036 |
| 2003/0055470 A1 | 3/2003 | Mon et al. | |
| 2005/0197715 A1* | 9/2005 | Kugler | A61B 17/0401 623/23.65 |
| 2007/0233170 A1* | 10/2007 | Gertner | A61B 17/0401 606/192 |
| 2008/0177398 A1 | 7/2008 | Gross et al. | |
| 2009/0131959 A1* | 5/2009 | Rolland | A61F 2/04 606/158 |
| 2010/0121161 A1 | 5/2010 | Robertson | |
| 2011/0087337 A1* | 4/2011 | Forsell | A61B 17/12 623/23.68 |
| 2011/0196504 A1* | 8/2011 | Imran | A61F 2/04 623/23.64 |
| 2012/0089236 A1* | 4/2012 | Errico | A61F 2/04 623/23.68 |
| 2013/0013084 A1* | 1/2013 | Birk | A61F 5/0079 623/23.68 |
| 2014/0163664 A1* | 6/2014 | Goldsmith | A61B 17/00491 623/1.11 |
| 2016/0135942 A1 | 5/2016 | Drager et al. | |
| 2016/0143723 A1* | 5/2016 | Imran | A61F 2/04 623/23.67 |
| 2016/0278944 A1* | 9/2016 | D'Lima | A61F 2/4657 |

OTHER PUBLICATIONS

Electrical Stimulation for Bladder Emptying (and Enhancing Volumes) [online]; [retrieved on Jul. 28, 2016]; Retrieved from http://www.scireproject.com/rehabilitation-evidence/bladder-management/desd-therapy-in-sci/enhancing-I.

Implantable Bladder Senors: A Methodological Review [online]; [retrieved on Jul. 28, 2016]; Retrieved from http://www.ncbi.nlm.nih.gov/pmc/articles/PMC4582084/pdf/inj-19-3-133.pdf.

Implanted Bladder Stimulator [online]; [retrieved on Jul. 28, 2016]; Retrieved from https://www.chrp.org/empowering/ibs.shtm.

Mahfouz, W. et al. "Normal Urodynamic Parameters in Women. Part II. Invasive Urodynamics." in International Urogynecology Journal (Mar. 2012), 23:269-277. DOI 10.1007/s00192-011-1585-y.

Management of Urinary Problems Caused by Spinal Cord Injury [online]; [retrieved on Jul. 28, 2016]; Retrieved from http://sci.washington.edu/info/forums/reports/urinary_problems.asp.

* cited by examiner

SYSTEMS AND METHODS FOR ASSISTING PATIENTS IN EMPTYING THEIR BLADDER EFFICIENTLY

CROSS-REFERENCE TO RELATED APPLICATIONS

This application is a continuation of U.S. patent application Ser. No. 15/297,727 filed Oct. 19, 2016, which claims the benefit of U.S. Provisional Patent App. No. 62/368,401 filed on Jul. 29, 2016, incorporated herein by reference.

FIELD OF THE DISCLOSURE

The present disclosure relates generally to systems, components, devices and methods for assisting a patient to efficiently empty a weakened or paralyzed bladder or a neobladder.

BACKGROUND

The bladder or urinary bladder is a muscular sac in the pelvis, located just above and behind the pubic bone. Urine is made in the kidneys, and travels down two tubes called ureters to the bladder. In normal operation, the bladder muscles stretch to allow the bladder to store urine. When desired, a person can normally voluntarily urinate. In a healthy condition, during urination the bladder muscles contract and two sphincters (valves) open to allow urine to be expelled. In both males and females, urine exits the bladder into the urethra, which carries urine out of the body.

Bladder paralysis can occur from compression of the spinal nerves roots, a condition called Cauda Equina syndrome. These nerve roots normally cause the bladder to contract. Cauda equine syndrome can be caused by a severe ruptured disk in the lumbar area, severe lumbar spinal stenosis, spinal injury from a fall, motor vehicle accidents, gunshot wounds, or infection. Also, a weakened bladder or a need for bladder removal can be due to bladder cancer. Bladder cancer is the fourth most common cancer in men and the tenth in women with an estimated 68,000 cases in the U.S. annually. Weak bladder can also occur from other medical conditions.

Many patients with bladder cancer eventually need to have the bladder removed, e.g. a cystectomy. Often the surgeon then creates a new bladder, referred to as a neobladder, from the patient's small intestine. Patients with reconstructed bladders after cystectomy are often unable to empty the neobladder because of a lack of muscle tissues inside the neobladder.

After a total cystectomy, the surgeon works to reconstruct the urinary tract in order to allow urine to leave the body. The surgeon has one of the following options:
1. He may use a piece of the patient's intestine to create a tube to run from the kidneys to the abdominal wall (Heal conduit or urostomy). The urine is collected in a bag worn on the abdomen.
2. A second option is what is called cutaneous continent urinary diversion (Indiana pouch). In this option, the operator creates a reservoir to the urine attached to the abdominal wall. The patient has to pass a catheter through the abdominal wall opening several times a day to empty the pouch.
3. A third option is what is called orthotopic continent diversion (Neobladder). The created pouch in this case is attached to the urethra. The patient will be able empty the bladder in a relatively normal fashion.

However, the process of voiding with a neobladder in reality is far from normal. The neobladder does not contract. The patient usually has to learn several techniques, such as pelvic exercises, to increase the pelvic pressure to help voiding. In most cases the void is incomplete, leaving residual urine which puts the patient at risk of recurrent UTI (urinary tract infection). Most patients have to use intermittent self-catheterization to fully void. Further, a neobladder does not supply the patient with a feeling of a bladder filling or fullness.

Studies have shown that normal individuals experience certain sensation patterns as the bladder fills, corresponding to increases in bladder pressure. Urodynamic studies in normal individuals show the following parameters; during the filling phase, abdominal and bladder pressures are recorded via rectal and urethral catheters, respectively, whereas detrusor pressure (Pdet) is calculated by subtracting abdominal pressure from bladder pressure. Initial resting abdominal and bladder pressures are 5-20 cm $H_2O$ in the supine position, 15-40 cm $H_2O$ in the sitting position, and 30-50 cm $H_2O$ in the standing position. Pdet in an empty bladder varies between 0 and 10 cm $H_2O$ in 90% of cases. Normal Pdet during bladder filling at a rate of 50-60 mils should be <20 cm $H_2O$.

There are three basic normal bladder sensation patterns: (a) the first sensation of bladder filling, which is felt when the volunteers first become aware of bladder filling (it is vague sensation, felt in the lower pelvis, which waxes and wanes, and could be easily ignored for few minutes); (b) first desire to void, a constant sensation that would lead the patient to void in the next convenient moment, but still voiding can be delayed (it is felt in the lower abdomen and gradually increases with bladder filling); and (c) strong desire to void, a persistent desire to void without fear of leakage, and felt in the perineum or urethra. The volume thresholds when the sensations are felt are generally lower in women.

There remains a need for an apparatus which creates awareness of bladder fullness and gives the patient full control to void normally.

SUMMARY

The current disclosure relates to systems, components, devices and methods which assist a patient in feeling the fullness of his or her bladder and permit him/her to empty his/her bladder by the push of a button. The system is implanted, and in brief includes a bladder sensor and compression assembly, an actuator, and an electronic controller. Optional occluders can be included for the ureters or urethra. The system monitors bladder pressure and alerts the patient when there is a need to void the bladder, optionally with increasing alert levels. When desired, the patient can selectively activate the compression assembly using an actuator, such as an implanted on/off switch.

In certain embodiments, the compression assembly includes plates or blades assembled with electromagnetic portions and biasing mechanisms. When the electromagnets are energized, the plates are magnetically pulled together, compressing the bladder to assist in voiding. When the electromagnets are deactivated, the plates return to a separated position due to springs or a similar biasing mechanism.

In selected embodiments, a system is provided for assisting a patient to empty his or her bladder. The system includes a pair of plates arranged adjacent opposing walls of a patient's bladder. At least one pair of electromagnets is connected to the pair of plates and configured to generate an attractive force between them when energized, wherein the attractive force pulls the plates inward to compress the bladder. A biasing mechanism is connected to the plates and configured to separate the plates when the electromagnets are deactivated. An actuator is coupled to the electromagnets and selectively triggerable by the patient to selectively energize the electromagnets. The system may also include a bladder pressure sensor implanted to sense the pressure in the patient's bladder and to report the pressure reading, and an alert mechanism to alert the patient when the bladder pressure reading exceeds a predetermined threshold. Optionally, the alert mechanism is configured to provide a plurality of alert levels correlating to the bladder pressure reading successively exceeding a corresponding plurality of predetermined thresholds.

Further embodiments encompass a system for assisting a patient to empty his or her bladder, including a controller implanted in a patient. A bladder pressure sensor is implanted in the patient's bladder to sense the pressure in the patient's bladder and to report the pressure reading to the controller. A compression assembly is implanted around the patient's bladder and operably coupled to the controller. The compression assembly includes a pair of plates arranged adjacent opposing walls of a patient's bladder and at least one pair of electromagnets associated with the pair of plates, wherein when the electromagnets are energized an attractive force is generated between them, pulling the plates together and compressing the bladder. The system includes an alert mechanism operatively coupled to said controller. The controller is configured to activate the alert mechanism to alert the patient when the bladder pressure reading exceeds a predetermined threshold. An actuator is operatively coupled to the controller and is configured to be selectively triggered by the patient, and operates so that the compression assembly compresses the bladder when the patient triggers the actuator.

Optionally, the system includes a biasing mechanism connected to the plates and configured to separate the plates when said electromagnets are deactivated. The alert mechanism may provide a plurality of alert levels to the patient correlating to the bladder pressure reading successively exceeding a corresponding plurality of predetermined thresholds. The alert mechanism may be an implanted vibrator.

In selected embodiments, the biasing mechanism includes at least one compression driver arranged between the plates. The compression driver is biased, for example with one or more springs, to separate the plates when said electromagnets are deactivated.

In certain embodiments, the system includes at least one occluder arranged around a ureter or the urethra. The occluder may be operable between an open position and a closed position, where the occluder seals the ureter or urethra in the closed position. In some embodiments, the occluder may incorporate an electromagnet and a movable plate.

Objects, features and advantages of the present disclosure shall become apparent from the detailed drawings and descriptions provided herein.

DESCRIPTION OF DISCLOSED EMBODIMENTS

For the purposes of promoting an understanding of the principles of the disclosure, reference will now be made to the embodiments illustrated and specific language will be used to describe the same. It will nevertheless be understood that no limitation of the scope of the disclosure is thereby intended, such alterations, modifications, and further applications of the principles of the disclosure being contemplated as would normally occur to one skilled in the art to which the disclosure relates.

The current disclosure relates to an implantable system, devices, components and methods which assist a patient in feeling the fullness of his or her bladder and permit him/her to empty his bladder by the push of a button. The present system overcomes many of the shortcomings of previous methods and devices. As examples:

It provides a fully implantable system that allows voiding to be near normal without any need for special pelvic exercises and training.

It provides sensory input to the patient at different phases of bladder filling. This will allow the patient to choose the convenient time to void.

It provides a control switch, which the patient may push easily and discreetly, without being noticed by any observer.

It provides an easily made dependable compressor that can be easily implanted and mounted on the bladder wall or its mesentery.

It provides a safety emergency shut off and warning to the patient in case of urine outflow obstruction.

It provides an option of preventing ureteral reflux by temporarily occluding the ureters when the patient is voiding.

It provides an option for preventing urine leak by occluding the urethra when the bladder pressure reaches a preset threshold.

It provides simple components of the device that are already present in the market and used for different purposes, like the cardiac pace maker, AICD (Automated implantable Cardiac defibrillator).

Figure 1:
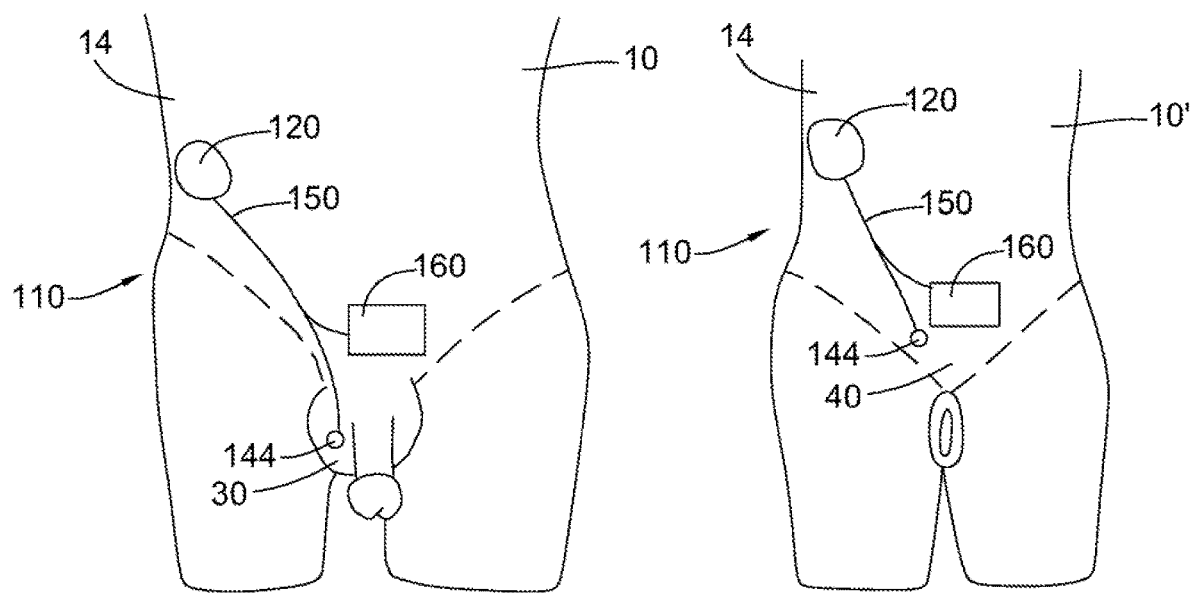
FIG. 1 is an illustration of an example embodiment of a system in a representative male body or alternately in a female body.
Figure 3:
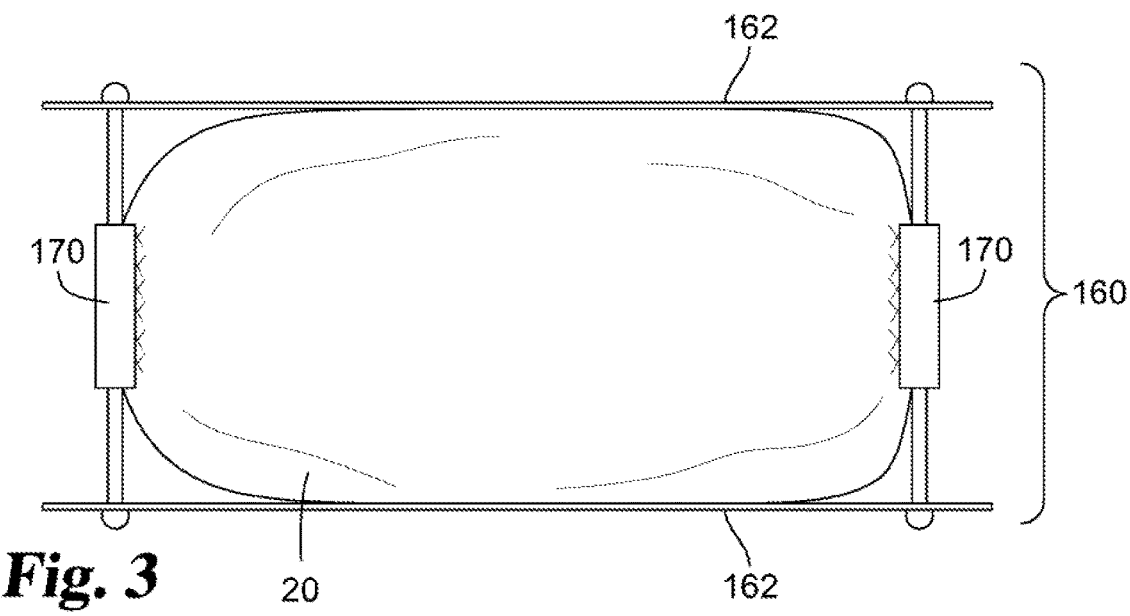
FIG. 3 illustrates a compression assembly usable with the system illustrated in FIG. 1

The system 110 is illustrated in a representative male body 10 or alternately in a female body 10' in FIG. 1. The disclosure herein is applicable to both males and females. Gender pronouns are not intended to be limiting. The system 110 is primarily implanted, and in brief includes a bladder sensor and compression assembly 160, an actuator 144, and an electronic controller 120. Optional occluders can be included for the ureters or urethra. An external programming device can also be used to monitor, program and control the system. The bladder sensor and compression assembly 160 is mounted around the bladder 20 (FIG. 3). A preferred site for implanting the electronic controller 120 is below the skin of the lateral abdominal wall 14. The patient can activate voiding using an actuator 144, such as an implantable on/off switch. As examples, actuator 144 may be a toggle or push-button switch. An example location for the switch is the scrotum 30 in men and the pubic area 40 in women. The actuator 144 is operatively attached to the controller 120 and the bladder sensor and compression assembly 160 via one or more cable portions 150 tunneled under the skin. Typically, laparotomy or laparoscopic surgery is performed to implant the compression assembly 160 around the bladder wall or its mesentery. The actuator 144 may be implanted in the scrotum 30 or in the pubic area 40 under the skin using the same laparotomy/laparoscopic incision.

A pressure sensor/transducer is attached to the bladder or neobladder wall and senses the bladder pressure as it fills. In operation, when the pressure reaches one or more predetermined pressure thresholds the controller alerts the patient, such as by activating a vibrator, optionally with increasing alert levels. When the patient is alerted, the patient may selectively activate the actuator to void the bladder. As the patient voids, the bladder pressure drops and the alert is discontinued.

Figure 2:
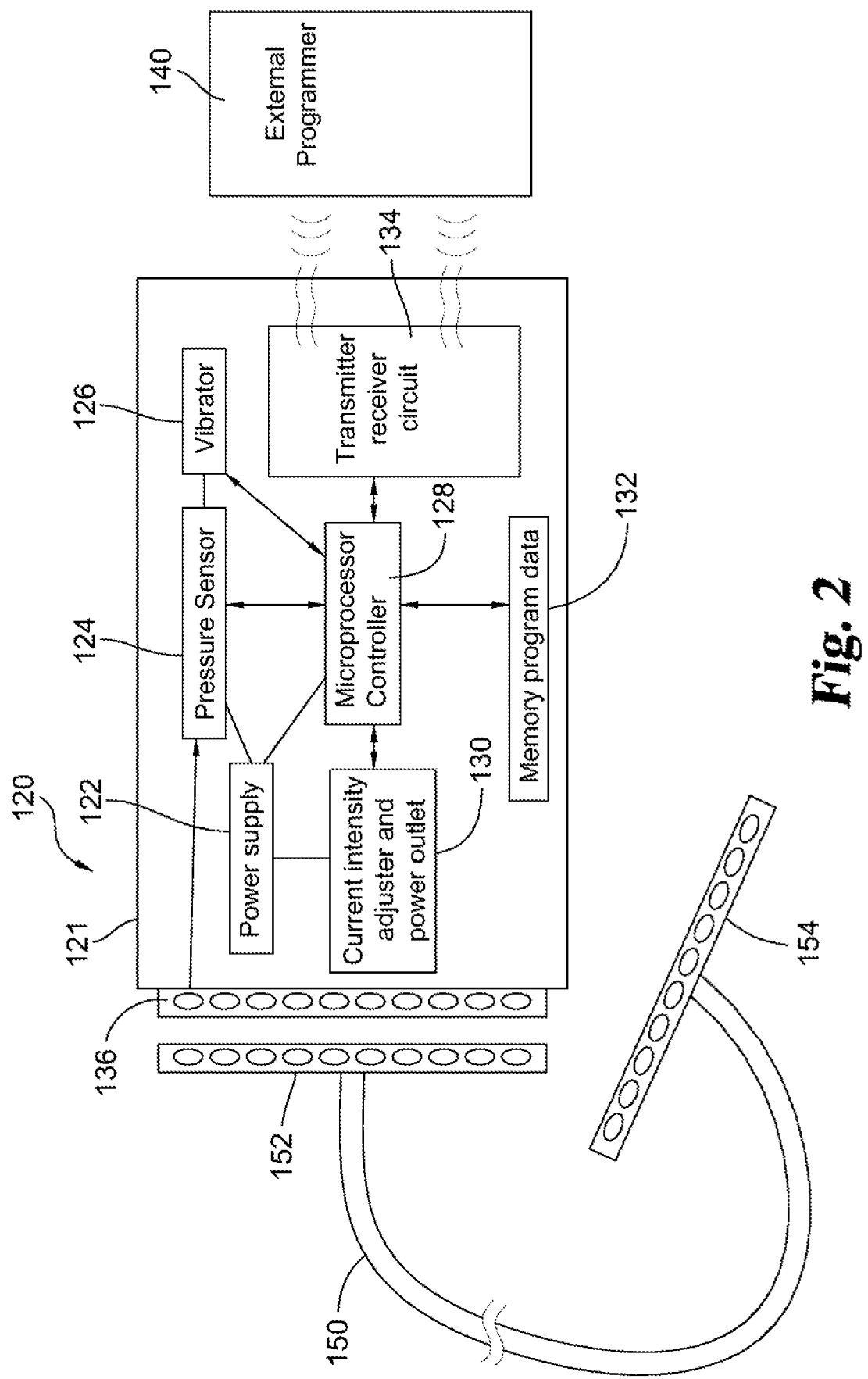
FIG. 2 schematically illustrates a controller usable with the system illustrated in FIG. 1.

An example embodiment of an electronic controller 120 is schematically illustrated in FIG. 2. The controller 120 may be implanted by a surgical procedure under the skin of the abdominal wall 14, preferably the lateral side. Alternately, the controller can be implanted at any location preferred by the patient and/or the surgeon. It can be implanted for instance in the thigh under the skin.

Controller 120 includes a housing 121 which contains various operatively connected elements, such as a power supply 122, a pressure sensor circuit 124, an alert mechanism such as a vibrator 126, a processor 128, a memory and/or data storage media 132, a current regulator 130, a transmitter/receiver 134 for communicating with an external programmer device 140, and an external interface 136 such as an electrical connector. Processor 128 may be a microprocessor or other suitable control circuitry configured to accept sensor input and calculate control output signals. The housing 121 includes typical aspects of implantable devices, such as being made of non-toxic and preferably bio-compatible materials such as Titanium or any different alloy. The shape of housing 121 is preferably a rounded oval or semi-oval to prevent any potential pressure erosion from sharp corners.

The power supply 122 may typically be a sealed and portable power supply such as a battery. The battery may be a long-life battery, or alternately may be rechargeable using wired or wireless external charging methods, such as wireless induction. The current regulator 130 controls and modifies the intensity of the electric current and power supplied from the power supply 122 to the compression assembly 160, and specifically to the electromagnets, discussed hereafter. If the current is moderate the bladder compression will be moderate and gradual allowing more natural voiding.

Pressure sensor circuit 124 receives a pressure reading from the implanted pressure sensor and communicates with processor 128 to compare the pressure reading with the data stored in the memory media 132. The pressure data can also be stored in memory media 132. When the pressure reading reaches one or more thresholds, the controller activates the patient alert mechanism such as vibrator 126.

The pressure readings, threshold levels, alert and control signal data can be entered, modified, monitored and/or controlled via wireless communication between transmitter/receiver 134 and an external programmer device 140. The external programmer device 140 can be also used to remotely activate emptying the bladder and to control any occluders. The external programmer device 140 can be a device such as a remote control, a personal mobile electronic device or a computer, and may be operated by the patient or a medical care giver.

The patient alert mechanism is arranged to alert the patient when activated. In some embodiments, a vibrator 126 is located under the patient's skin so that the patient can readily feel the vibrations when the vibrator is activated. A vibrator 126 is illustrated as located inside the housing of the controller, yet alternately it could be implanted separately and operatively connected to the controller. Still alternately, the vibrator 126 could be external to the patient's body and, for example, worn adjacent the patient's skin such as on a belt, watch, necklace or bracelet. Further, the alert mechanism may alternately be or include other patient alert methods such as lights, sounds, or on-screen alerts and can be discreetly brought to the patient's or a care giver's attention using alternate signal receiving devices, for example using a mobile phone, a watch, a tablet, a computer, jewelry or other device.

The controller 120 is operably coupled to the other system components, for example via one or more cable portions 150 tunneled under the skin. Cable 150 includes a proximal end 152, with a connector which mates with controller interface 136. The distal end 154 may be formed of one or more cable portions which may diverge to connect to the compression assembly 160, the actuator 144, the pressure sensor and any occluders if present. In some embodiments, a single cable with multiple distal ends may be used. Alternately, multiple cables may be used and/or other communication methods may be used to operably couple the components, such as wireless signals.

A pressure sensor/transducer is attached to the bladder/neobladder wall and senses the bladder pressure as it fills. The pressure sensor is preferably attached to the bladder wall, but it may be implanted in the inner surface of the bladder under the mucosa. The sensor is attached to controller 120 via electrical cable 150. The sensor's pressure reading is compared with preset parameters stored in processor 128. When the pressure reaches one or more predetermined thresholds, the controller activates the alert mechanism appropriately. The pressure at which the alert is activated is determined by the surgeon, for example using external programmer device 140. In certain embodiments three phases of low, medium and strong alerts are used, correlating with successive natural feelings associated with the bladder filling, namely: awareness of the bladder filling, a first desire to void, and a strong desire to void. The alert level style such as the vibration pattern and intensity can correlate with these phases. For example; the vibration may be intermittent and soft in the first phase, intermittent and stronger in the second phase, and continuous and even stronger in the third phase.

Figure 4A:
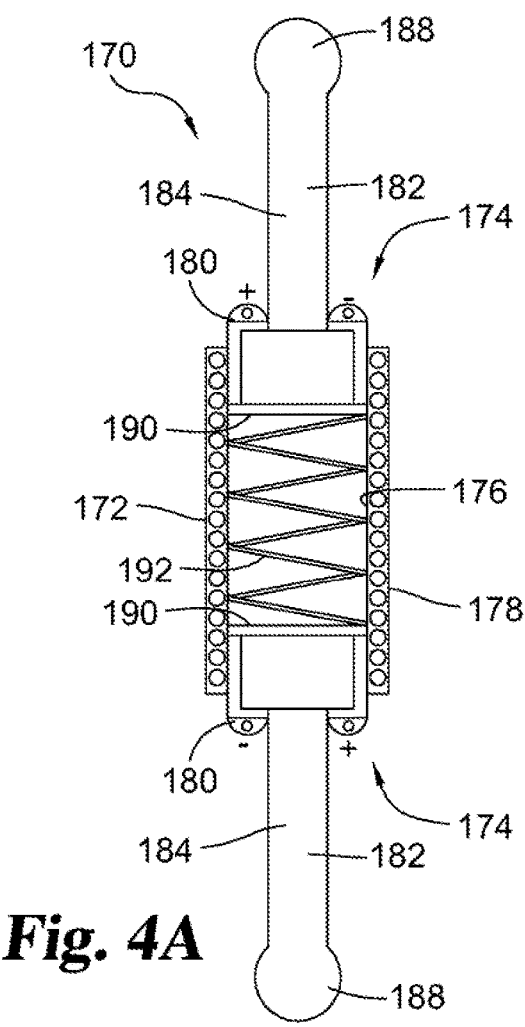
FIGS. 4A and 4B illustrate cross-sectional views in expanded and contracted positions of an embodiment of a driver unit usable in the compression assembly illustrated in FIG. 3.
Figure 4B:
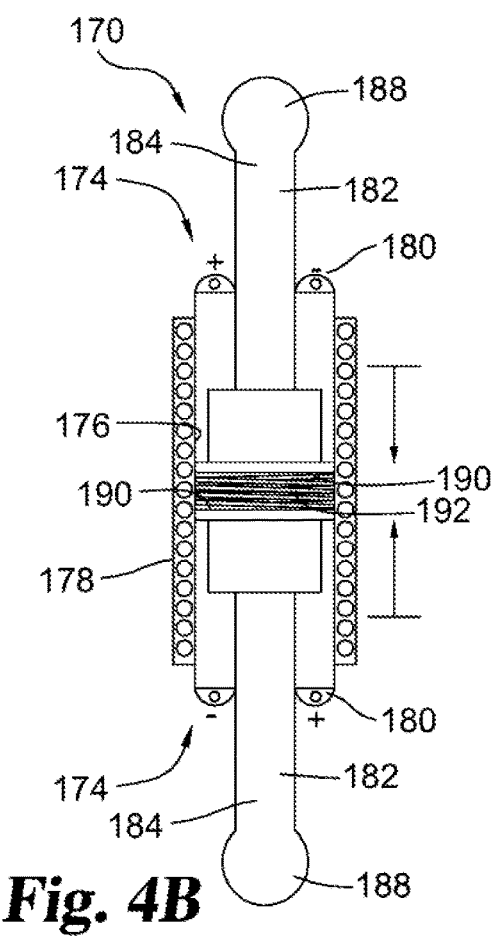
Figure 5:
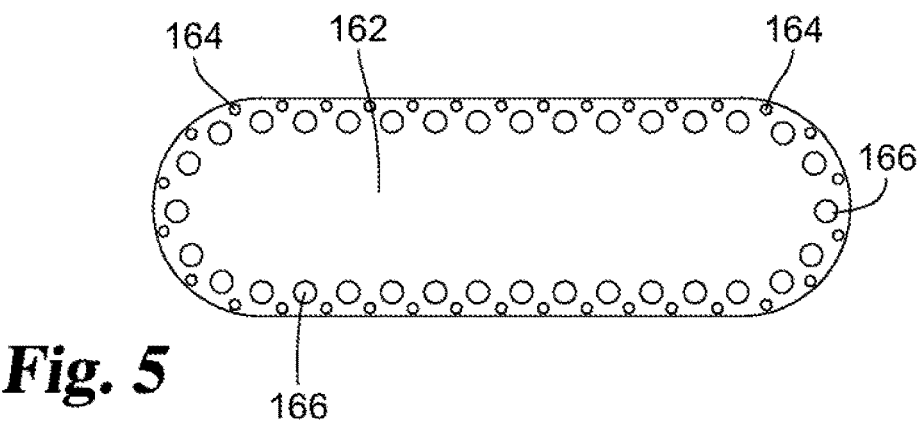
FIG. 5 illustrates a plate usable in the compression assembly illustrated in FIG. 3.

FIG. 3 illustrates a general view of the compression assembly 160 mounted around the bladder 20. Example components are illustrated in FIGS. 4A, 4B & 5. The pressure sensor/transducer (not illustrated) is implanted with bladder 20 and may be part of assembly 160. Compression assembly 160 includes a pair of compression plates or blades 162 arranged adjacent opposing walls of the bladder 20. One or more compression drivers 170 are arranged between plates 162. Drivers 170 may be equally or non-uniformly spaced around assembly 160 as desired to provide a desired compression loading profile. One, two, four or other numbers of drivers may be used. When activated, the drivers 170 pull the plates 162 toward each other, squeezing the bladder 20 between the plates. The drivers 170 are biased to extend to separate the plates 162 when the electromagnets are deactivated, such as when voiding is complete.

FIGS. 4A and 4B illustrate an example compression driver 170 in an extended position (FIG. 4A) and a compressed position (FIG. 4B). Driver 170 comprises an envelope or a housing 172 with a non-friction or low friction inner wall 176. Housing 172 is preferably compressible. The housing outer wall 178 may include an edge with multiple small holes to allow the unit to be attached to the bladder, for example via stitching. Housing 172 includes opposing ends 174.

A pair of plungers 182 extend from opposing ends 174. In certain alternate embodiments, a driver with only one plunger may be used. Plungers 182 each include a shaft 184. An inner end of each shaft 184 within housing 172 includes an electromagnet 190. An outer end of each shaft includes a connector, such as a compressible ball 188. A biasing mechanism, such as at least one spring 192, is arranged within housing 172 between respective plunger bearing surfaces, such as end plates of electromagnets 190.

When electromagnets 190 are energized, the attractive force compresses spring 192 as the plungers 182 move inward. Preferably, the amount of the magnetic force should continuously be slightly higher than the pulling force of the spring to allow smooth, gentle compression and a continuous gentle stream of urine to be expelled. The power and pulling force applied may be increased during the course of the compression step in order to remain higher than the increasing force as the spring is compressed. The biasing mechanism is arranged to extend plungers 182 outward to a resting position when the electromagnets are deactivated. In other embodiments, the biasing mechanism may use a compressible fluid or gas instead of a spring to return the plungers to the resting position.

FIG. 5 illustrates a plan view of an example compression plate 162. In some embodiments, it is made of a metal such as titanium or a titanium alloy such as nitinol. In other embodiments it may be a polymeric material. It can be made of any sufficiently rigid non-toxic, bio-compatible material suitable for implantation in human or animal tissue. Optionally a pad can be arranged between the plate and the bladder surface. The shape is preferably oval with smooth rounded ends. The edges of plate 162 may include two types or series of holes. The smaller holes 164 may allow the plate 162 to be secured in place on the bladder wall or its mesentery using stitches. The larger holes 166 may have the same diameter as the cross-section of the plunger shaft 184.

An end of each driver 170, such as compressible ball 188, is engaged to plate 162. In some embodiments, the compressible ball 188 is arranged on an outward side of plate 162, opposite to the bladder. The ball 188 and hole 166 may form a partially spherical nest, allowing the plunger to rotate slightly relative to plate 162. In some embodiments, ball 188 is compressed while being introduced through hole 166, and then expands to prevent disengagement. In an alternate embodiment, a key and key-hole arrangement may be used to allow a driver end to be placed through plate 162 when aligned, then rotated out of alignment to inhibit the end from disconnecting from plate 162. Alternate driver to plate engagement mechanisms may instead be used. When the drivers 170 are activated, opposing plates 162 are pulled inward to compress bladder 20, and correspondingly compress spring 192. When the drivers 170 are deactivated, spring 192 extends plungers 182, driving plates 162 to the extended position.

Figure 6A:
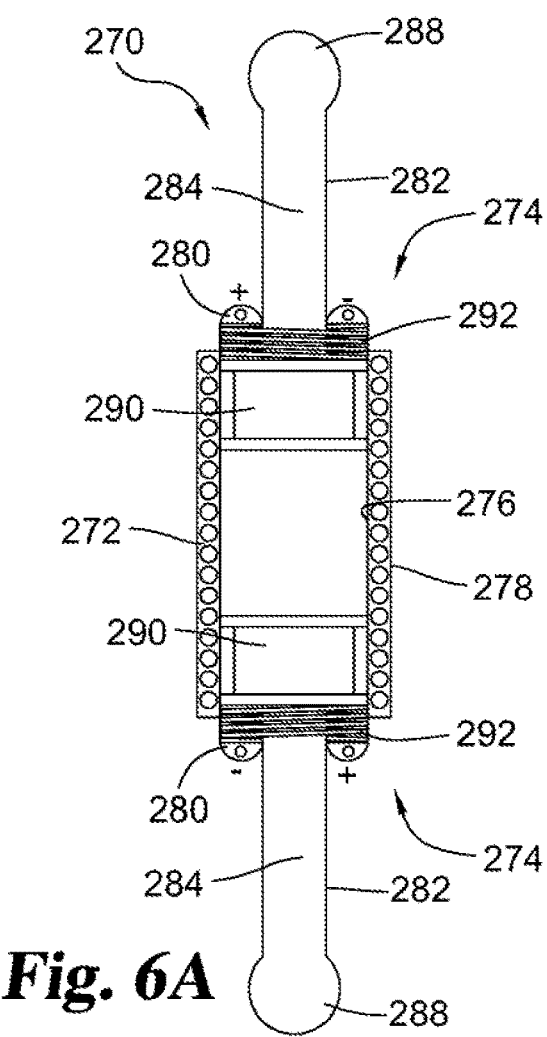
FIGS. 6A and 6B illustrate cross-sectional views of an alternate embodiment of a driver unit usable in the compression assembly illustrated in FIG. 3.
Figure 6B:
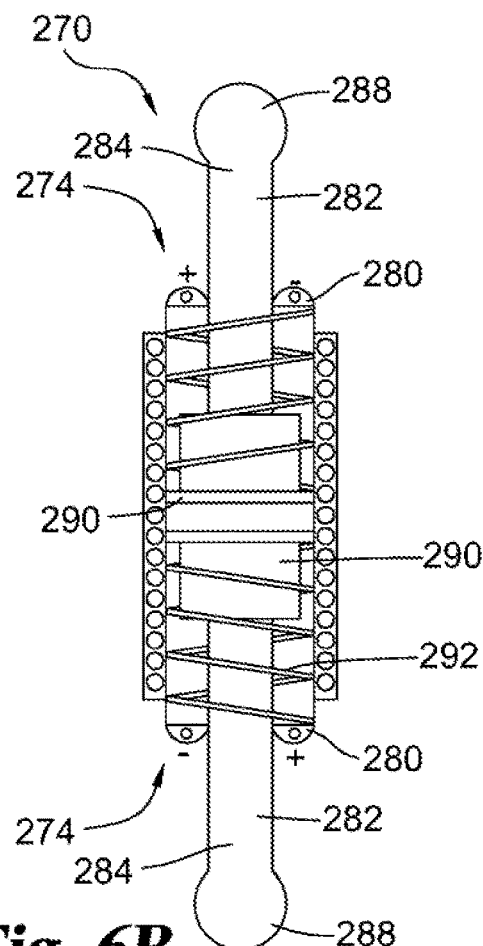

FIGS. 6A and 6B illustrate an alternate embodiment of a compression driver 270 in an extended position (FIG. 6A) and a compressed position (FIG. 6B). Driver 270 comprises an envelope or a housing 272 with a non-friction or low friction inner wall 276. Housing 272 is preferably compressible. The housing outer wall 278 may include an edge with multiple small holes to allow the unit to be attached to the bladder, for example via stitching. Housing 272 includes opposing ends 274.

A pair of plungers 282 extend from opposing ends 274. Plungers 282 each include a shaft 284. An end of each shaft 284 within housing 272 includes an electromagnet 290. An outer end of each shaft includes a compressible ball 288. When the electromagnets 290 are energized, an attractive force is generated, pulling the plungers 282 inward. A biasing mechanism, such as a pair of springs 292 is arranged within housing 272, for example each is attached between a respective bearing surface on each of opposing ends 274 and a respective electromagnet 290. When electromagnets 290 are energized, the attractive force expands springs 292. In this arrangement, the biasing mechanism is arranged to retract the springs to expand plungers 282 outward to a resting position when the electromagnets are deactivated.

Figure 7:
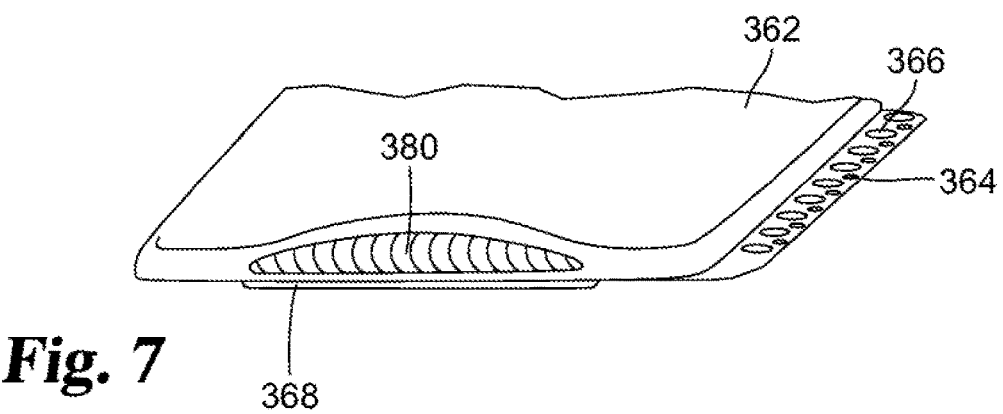
FIG. 7 illustrates a plate usable with an alternate compression assembly.
Figure 8:
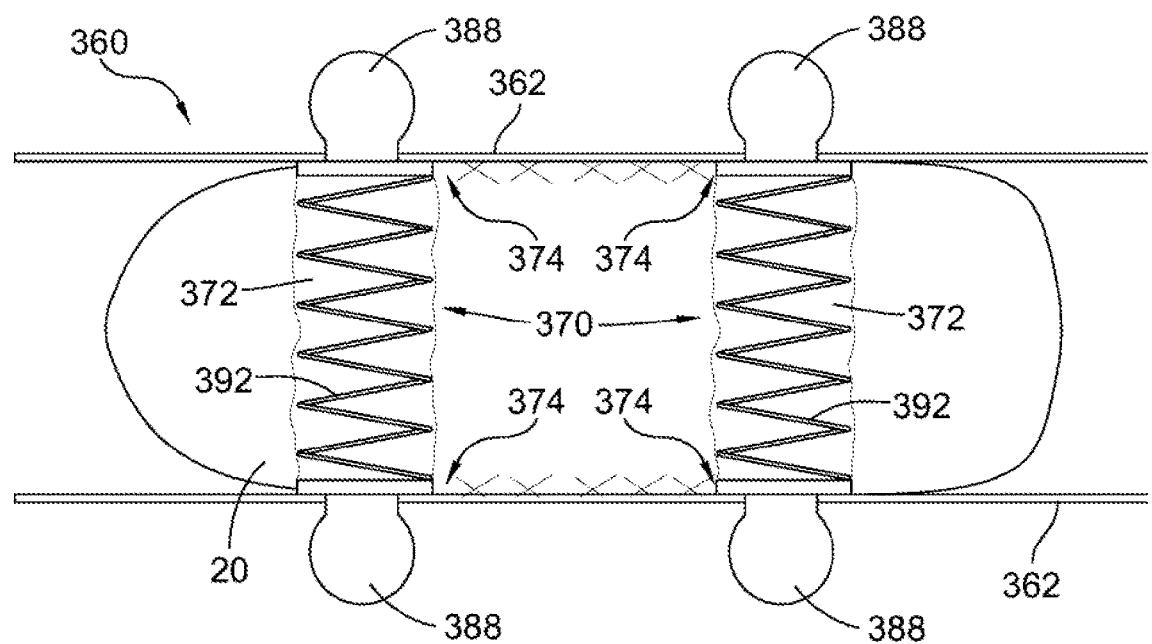
FIG. 8 illustrates an alternate compression assembly using the plate illustrated in FIG. 7.

FIGS. 7 & 8 illustrate an alternate embodiment of a compression assembly mountable around bladder 20. Compression assembly 360 includes a pair of compression plates or blades 362 arrangeable on opposing sides of the bladder. One or more compression drivers 370 are arranged between plates 362. When activated, the drivers 370 pull the plates 362 together, squeezing the bladder 20 between them. The drivers 370 are biased to extend to separate the plates 362 when deactivated, such as when voiding is complete.

Driver 370 comprises an envelope or a housing 372. Housing 372 is preferably compressible. The housing outer wall may include an edge with multiple small holes to allow the unit to be attached to the bladder, for example via stitching. Housing 372 includes opposing ends 374, each with a connector, such as a compressible ball 388 engaged to a respective plate 362.

FIG. 7 illustrates a perspective view of an example compression plate 362 usable in the assembly of FIG. 8. In some embodiments, it is made of titanium. However, it can be made of any sufficiently rigid non-toxic, bio-compatible and implantable material. Optionally, padding 368 may be arranged on the surface of plate 362 which will contact the bladder. The edges of plate 362 may include two types or series of holes. The smaller holes 364 may allow the plate 362 to be secured in place on the bladder wall or its mesentery using stitches. The larger holes 366 can be fastened to a driver 370, such as by a receiving a compressible ball 388. In this embodiment, an electromagnet 380 is mounted to or embedded within each plate 362.

When the electromagnets 380 are energized, an attractive force is generated between them, pulling the plates 362 inward and compressing bladder 20. A biasing mechanism, such as a spring 392 is arranged within each of the drivers 370. When electromagnets 380 are activated, the attractive force compresses springs 392. When the electromagnets 380 are deactivated, the biasing mechanism is arranged to extend drivers 370 and plates 362 outward to a resting position. In other embodiments, the biasing mechanism may use a compressible fluid or gas.

Figure 9A:
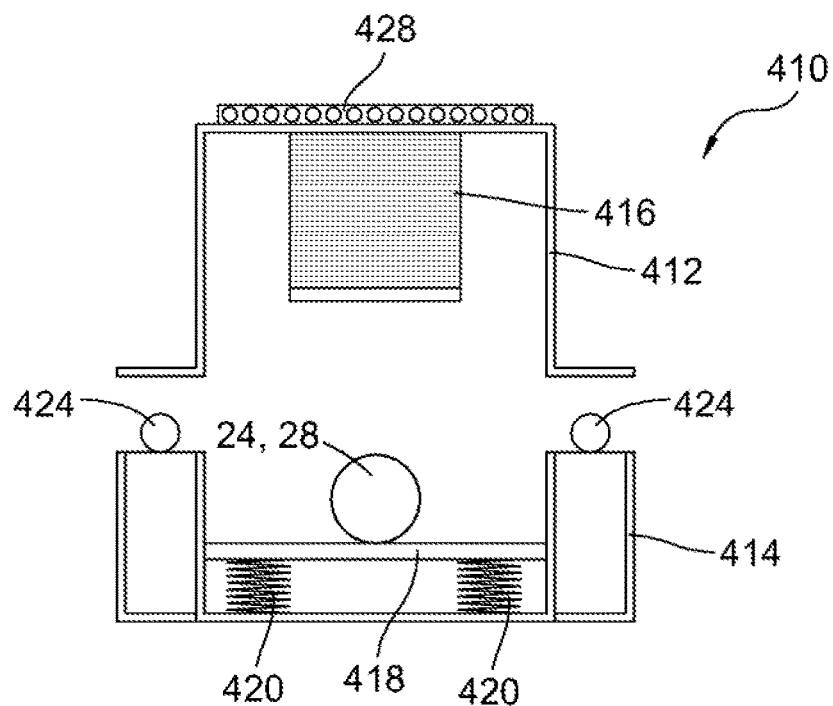
FIGS. 9A and 9B illustrate cross-sectional views in open and closed positions of an embodiment of an occluder usable with the system illustrated in FIG. 1.
Figure 9B:
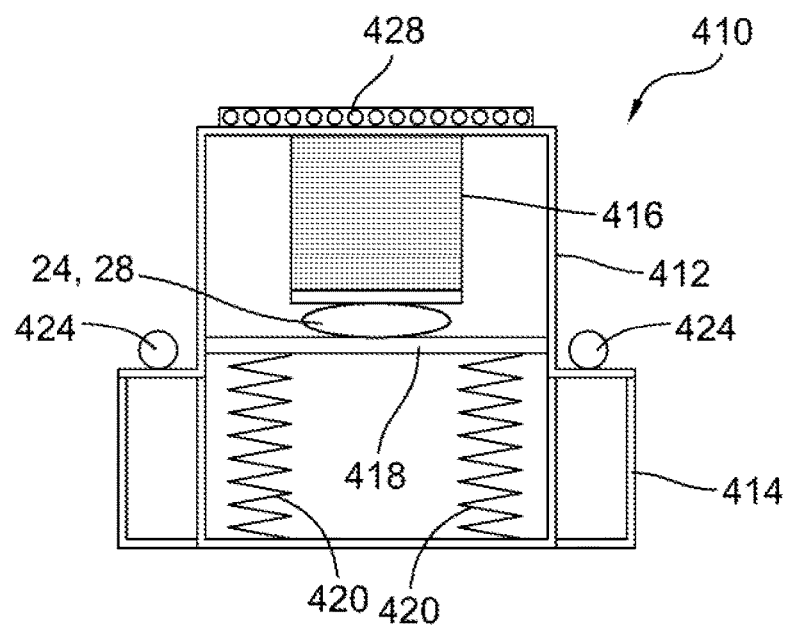

FIGS. 9A & 9B illustrate an embodiment of an optional occluder 410. One or more occluders can be used individually with one or both ureters 24 or urethra 28 to prevent undesired leakage through the urethra or reflux/backflow through a ureter. Occluder 410 is operably coupled to the controller and the occluder's operation may be controlled by the controller. FIG. 9A illustrates the occluder 410 in the open position, and FIG. 9B illustrates the occluder 410 in the closed position, where it engages and seals the corresponding ureter 24 or urethra 28. The structure and arrangement of the occluder 410 may be the same when used with either a ureter 24 or the urethra 28, although the operative logic may be reversed. For example, it may be desirable for the ureter 24 to be open when the urethra 28 is sealed or vice versa.

Occluder 410 includes two housing portions 412 and 414. Housing portions 412 and 414 are referred to as upper housing portion 412 and lower housing portion 414 for ease of reference, but without intending to be limited to a particular orientation in use. Upper housing portion 412 and lower housing portion 414 are arranged to encircle a respective ureter 24 or urethra 28, with the ureter/urethra 24, 28 passing through a central passage of occluder 410. The housing portions are attached to each other around the ureter or urethra, preferably by fasteners 424 such as a compressible ball or any click and go fastening method known in the art. The edge of each housing may have holes 428 to allow the occluder to be stitched to the surrounding tissue.

Upper housing portion 412 includes an electromagnet 416. Lower housing portion 414 contains a movable plate 418 inside the housing. Plate 418 is biased by one or more springs 420. Preferably, the plate 418 can move toward and away from electromagnet 416 with a minimum of friction against the walls of the housing. Occluder 410 may be arranged to be normally open, meaning the occluder is in the open position when not activated. Starting from a normally open position, when electromagnet 416 is energized, plate 418 is attracted by the magnetic force and moves towards the electromagnet to close the ureter or urethra 24, 28. When electromagnet 416 is deactivated, plate 418 is biased by retraction of springs 420 to return to the open, resting position by the spring force. Alternately, occluder 410 may be arranged to be normally closed, meaning the occluder is in the closed position when not activated. For example, springs 420 can bias plate 418 to the closed position, and plate 418 is repelled when electromagnet 416 is energized. In certain embodiments the plate and the lower end of electromagnet 416 are padded with rubber, silicone, or another soft material compatible with implantation to provide gentle compression.

The structure and arrangement of the occluder 410 may be the same when used with either the ureter 24 or urethra 28, although the operative logic may be reversed. When used around the urethra, the occluder may automatically close in response to an increase in bladder pressure at a certain threshold, and remains on until the patient triggers the actuator to void the bladder. When the bladder compressor assembly is turned on to empty the bladder, the urethral occluder is opened. Once the occluder is open it may not close again until the bladder pressure rises above a preset threshold, after the complete void. Alternately, a separate implantable switch may be provided to turn off the occluder. This is an additional safety option in case of any malfunction. The occluder switch may be implanted at a remote location from the actuator to prevent confusion. The external programmer may also have the option to remotely turn the urethral occluder on or off. It is preferable not to use a urethral occluder if other methods can be used to prevent incontinence.

When used around a ureter, the occluder may automatically close when the patient triggers the actuator to void the bladder. The occluder thus prevents ureteral reflux or backflow pressure of urine through the ureter. When the bladder compressor assembly is turned off, the ureter occluder is opened.

The system is preferably programmed to produce gradually increasing magnetic forces to gradually overcome the opposing forces produced by the springs. This gradually increasing force will allow a urine stream in voiding similar to a natural urine stream during normal voiding in healthy persons. It also prevents the bladder pressure from rising above a pressure point that might be interpreted by the sensor as an outlet obstruction.

To prevent over-distension incontinence the bladder pressure should not exceed the mean maximum urethral closure pressure, which is normally around 60 cm $H_2O$. If the bladder pressure exceeds an alarm level pressure threshold, for example due to a urethra outlet obstruction, the increased pressure triggers an emergency shut off of the compression assembly and activates a special alarm level alert, such as a vibration pattern alarming the patient to a problem. Shutting down compression helps prevent a possible bladder rupture. The patient may have to self-catheterize himself and/or seek medical attention to evaluate the problem.

Figure 10:
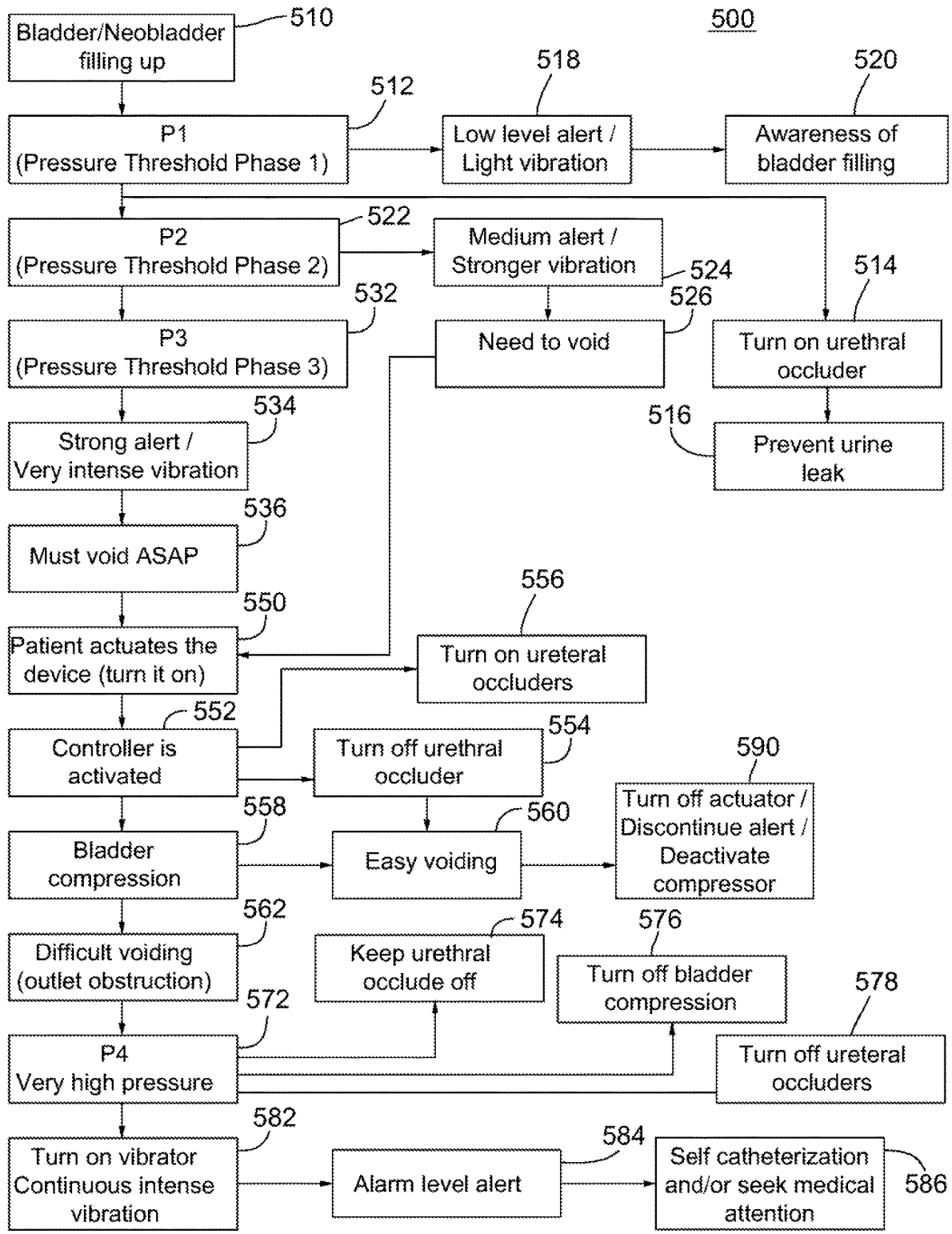
FIG. 10 illustrates a method of using the system illustrated in FIG. 1.

FIG. 10 displays a method 500 illustrating system 110 or a comparable system in operation. Once system 110 is implanted, the pressure sensor is configured to detect the bladder or neobladder filling with urine 510. When the pressure sensor detects that bladder pressure 512 exceeding a first pressure threshold P1, 512 the alert mechanism can provide a low level alert to the patient 518, such as light vibration, to convey initial awareness 520 to the patient. If present, the system may also signal the urethral occluder to close 514 to prevent urine leakage 516.

The bladder may continue to fill until the pressure sensor detects the bladder pressure reaching and/or exceeding a second pressure threshold P2, 522. When pressure threshold P2 is reached, the alert mechanism can provide a medium level alert to the patient 524, such as a stronger vibration, to convey a need to void 526 to the patient.

If the bladder is not voided, the bladder may continue to fill until the pressure sensor detects the bladder pressure reaching and/or exceeding an third or urgent pressure threshold P3, 532. When pressure threshold P3 is reached, the alert mechanism can provide a stronger level alert to the patient 534, such as an intense vibration, to convey an urgent need to void 536 to the patient.

When the patient is ready to void the bladder, the patient can then use the actuator to trigger the voiding process 550. Triggering the actuator signals the controller 552 to initiate bladder compression 558. If present, the controller may also turn off an urethral occluder 554 and may turn on any ureteral occluders 556. When voiding is complete or when desired, the patient may use the actuator to end the voiding process 590, which includes deactivating bladder compression and discontinuing the alert. The system then resets.

If there is difficulty voiding 562 such as due to a urethral obstruction, the bladder may continue to fill until the pressure sensor detects the bladder pressure reaching and/or exceeding an alarm level pressure threshold P4, 572. If pressure threshold P4 is reached, the system attempts to minimize pressure on the bladder by maintaining a urethral occluder, if present, in the off state 574, deactivating bladder compression 576 and turning off any ureteral occluders 578. Additionally, the alert mechanism can provide an alarm level alert to the patient 584, such as a continuous vibration 582, to indicate a need for the patient to administer self-catheterization and/or to seek medical attention 586.

While the disclosure has been illustrated and described in detail in the drawings and foregoing description, the same is to be considered as illustrative and not restrictive in character, it being understood that only certain embodiments have been shown and described and that all changes and modifications that come within the spirit of the disclosure are desired to be protected.

What is claimed is:

1. A system for assisting a patient to empty his or her bladder, comprising:
    a. a controller implanted in a patient, said controller having a processor and a memory unit with data indicating a predetermined bladder pressure threshold stored in said memory unit;
    b. a bladder pressure sensor implanted to sense the pressure in the patient's bladder and to report the pressure reading to the controller;
    c. a compression assembly implanted around the patient's bladder and operably coupled to said controller, said compression assembly including a pair of plates arranged adjacent opposing walls of a patient's bladder wherein said plates are biased apart and are selectively movable toward each other to compress the bladder;
    d. an alert mechanism operatively coupled to said controller, wherein said alert mechanism is an implanted vibrator;
    e. wherein the processor compares the pressure reading with data stored in a memory unit wherein said controller activates said alert mechanism to provide a plurality of alert levels to the patient correlating to the bladder pressure readings successively exceeding a corresponding plurality of predetermined thresholds stored in said memory unit; and,
    f. an actuator operatively coupled to said controller wherein said actuator is configured to be selectively triggered by the patient, and wherein said compression assembly compresses the bladder when the patient triggers the actuator.

2. The system of claim 1, wherein said alert mechanism is adjacent to the patient's skin.

3. The system of claim 1, comprising at least one occluder arranged around a ureter or the urethra, wherein the occluder is operable between an open position and a closed position, and wherein the occluder seals the ureter or urethra in the closed position.

4. The system of claim 3 wherein said occluder comprises a movable plate within a housing wherein when said occluder is operated said movable plate compresses the ureter or urethra.

5. The system of claim 4, wherein said movable plate is biased to return the occluder to the open position.

6. The system of claim 3, wherein said occluder is configured to close when the bladder pressure reading exceeds a predetermined threshold.

7. The system of claim 3, wherein said occluder is configured to open when the bladder pressure reading exceeds an alarm alert level.

8. The system of claim 1, wherein the predetermined threshold at which the alert is activated is communicated to said memory unit using a programmer device external to the patient's body.

9. A system for assisting a patient to empty his or her bladder, comprising:
    a. a bladder pressure sensor implanted in the patient's bladder to sense the pressure in the patient's bladder;
    b. a compression assembly implanted around the patient's bladder and operably coupled to said bladder pressure sensor, said compression assembly including a pair of plates arranged adjacent opposing walls of a patient's bladder wherein said plates are biased apart and are selectively movable toward each other to compress the bladder;
    c. an alert mechanism operatively coupled to said bladder pressure sensor, wherein said alert mechanism is an implanted vibrator wherein said alert mechanism provides a plurality of alert levels to the patient correlating to the bladder pressure reading successively exceeding a corresponding plurality of predetermined threshold; and,
    d. an actuator operatively coupled to said compression assembly wherein said actuator is configured to be selectively triggered by the patient, and wherein said compression assembly compresses the bladder when the patient triggers the actuator.

10. The system of claim 9, wherein said alert mechanism is implanted adjacent to the patient's skin.

11. The system of claim 9, wherein said alert mechanism is external to the patient's skin.

12. The system of claim 11, wherein said alert mechanism is configured to be worn adjacent to the patient's skin as a watch or piece of jewelry.

13. The system of claim 9, wherein the predetermined threshold at which the alert is activated is communicated to the system using a programmer device external to the patient's body.

14. A system for assisting a patient to empty his or her bladder, comprising:
    a. a controller implanted in a patient, said controller having a processor, a memory unit with data indicating a predetermined bladder pressure threshold stored in said memory unit and a receiver to wirelessly receive data from an external programmer device;
    b. a bladder pressure sensor implanted to sense the pressure in the patient's bladder and to report the pressure reading to the controller;
    c. a compression assembly implanted around the patient's bladder and operably coupled to said controller, said compression assembly including a pair of plates arranged adjacent opposing walls of a patient's bladder wherein said plates are biased apart and are selectively movable toward each other to compress the bladder;
    d. an alert mechanism operatively coupled to said controller, wherein said alert mechanism is an implanted vibrator;
    e. wherein the processor compares the pressure reading with data stored in a memory unit wherein said controller is configured to activate said alert mechanism to alert the patient when the bladder pressure reading exceeds the predetermined threshold; and,
    f. an actuator operatively coupled to said controller wherein said actuator is configured to be selectively triggered by the patient, and wherein said compression assembly compresses the bladder when the patient triggers the actuator.

* * * * *